US006815683B2

(12) United States Patent
Federici et al.

(10) Patent No.: US 6,815,683 B2
(45) Date of Patent: Nov. 9, 2004

(54) TERAHERTZ IMAGING SYSTEM AND METHOD

(75) Inventors: John Federici, Westfield, NJ (US); Robert Barat, Franklin Park, NJ (US); Dale E. Gary, Berkely Heights, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 10/444,577

(22) Filed: May 23, 2003

(65) Prior Publication Data

US 2004/0065831 A1 Apr. 8, 2004

Related U.S. Application Data

(60) Provisional application No. 60/384,762, filed on May 31, 2002.

(51) Int. Cl.[7] .............................................. G01N 21/00
(52) U.S. Cl. ...................... 250/341.1; 250/330; 250/340
(58) Field of Search .......................... 250/341.1, 358.1, 250/330, 340

(56) References Cited

U.S. PATENT DOCUMENTS

| | | | |
|---|---|---|---|
| 5,293,213 A | | 3/1994 | Klein et al. |
| 5,401,953 A | | 3/1995 | Spencer et al. |
| 5,623,145 A | | 4/1997 | Nuss |
| 5,710,430 A | * | 1/1998 | Nuss ........................ 250/358.1 |
| 6,078,047 A | | 6/2000 | Mittleman et al. |
| 6,144,679 A | | 11/2000 | Herman et al. |
| 6,320,191 B1 | | 11/2001 | Rudd |

FOREIGN PATENT DOCUMENTS

| | | |
|---|---|---|
| GB | 2350673 | 12/2000 |
| GB | 2359716 | 8/2001 |

OTHER PUBLICATIONS

Mittleman et al., T–Ray Imaging, IEEE Journal of Selected Topics in Quantum Electronics Sep. 1996, pp. 679–692, vol. 2, No. 3.
Mittleman et al., Recent Advances in Terahertz Imaging, Applied Physics B, Apr. 1999.
Johnson et al. Interferometric Imaging with Terahertz Pulses, IEEE Journal of Selected Topics in Quantum Electronics, Jul./Aug. 2001, pp. 592–599, vol. 7, No. 4.

* cited by examiner

Primary Examiner—Constantine Hannaher
Assistant Examiner—Timothy Moran
(74) Attorney, Agent, or Firm—Klauber & Jackson

(57) ABSTRACT

THz imaging apparatus and methods are provided for rapidly and effectively examining a region of interest to determine the presence of specified compositions. The apparatus includes means for generating electromagnetic radiation of a desired terahertz frequency suitable for the examination, and for rendering the radiation incident at the region of interest. Detector means are provided at a plurality of points in a plane spaced from the region of interest, for detecting the terahertz radiation reflected from or transmitted through the region. Means are provided for converting the detected terahertz radiation to an image of the region of interest from which the presence of the specified compositions are determinable.

20 Claims, 4 Drawing Sheets

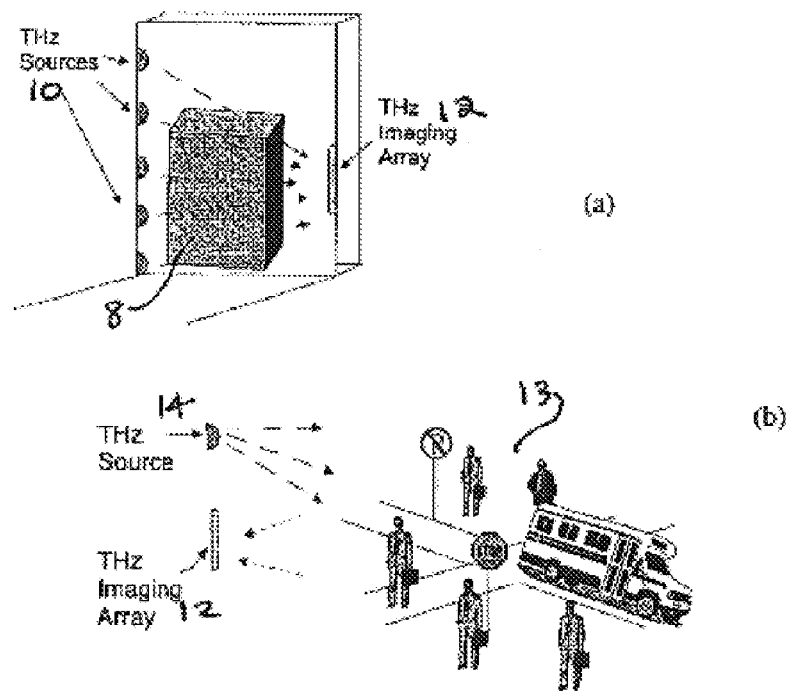
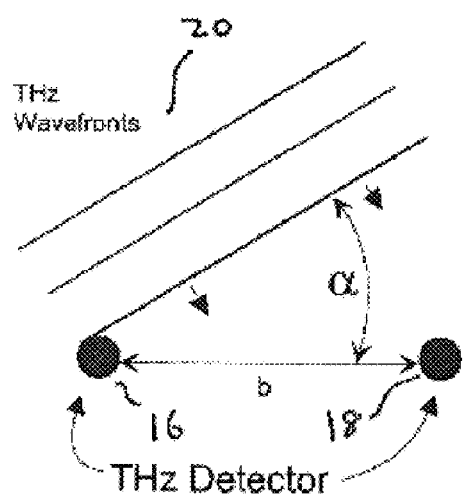
FIGURE 2

(a)

(b)

Arrangement of antennas in array 5 antennas in line; coordinates: 0, 1a, 3a, 7a, 16a
Provides baselines: 1, 2, 3, 4, 6, 7, 9, 13, 15, 16 x a

TERAHERTZ IMAGING SYSTEM AND METHOD

RELATED APPLICATION

This Application claims priority from U.S. Provisional Patent Application No. 60/384,762 filed May 31, 2002.

GOVERNMENT RIGHTS

The research leading to the present invention was supported, in part by the U.S. Army through an STTR grant (DAAD19-02-C-0085) and an SBIR grant. Additional support was provided through the National Science Foundation's SGER/REU grants (CTS-0233582). Accordingly, the United States Government may have certain rights in the invention.

FIELD OF THE INVENTION

This invention relates generally to imaging apparatus and methods, and more specifically relates to imaging systems and methods which utilize electromagnetic radiation in the Terahertz (THz) range as incident energy at objects to be examined.

BACKGROUND OF THE INVENTION

The present invention is directed toward detection of weaponry concealed on the person, or in containers such as suitcases, briefcases, sealed packages, or cartons. Such weaponry can include metallic devices such as handguns, but the invention especially addresses the issue of monitoring, detecting and characterizing concealed explosives and biological weapons.

As plastique explosives, fertilizer bombs and biological agents increasingly become weapons of war and terrorism, effective means for rapid detection and identification of concealed caches of these agents is increasingly imperative. One proposed solution is to use terahertz (THz) electromagnetic waves to spectroscopically detect and identify concealed explosives and biological weapons through their characteristic transmission or reflectivity spectra in the THz range (0.1–10 THz). Explosives (e.g. C-4, HMX, RDX, TNT, naphthalene, and ammonium nitrate) all have characteristic reflection and absorption spectra in the 0.1–2.0 THz range (100–2000 GHz, 3–0.15 mm) which are easily distinguishable from other materials such as human skin. In essence, explosives appear as different "colors" to the THz detector as compared to non-hazardous items. The use of THz for the detection of biological weapons has also shown great promise. Using THz spectroscopy it is therefore possible to in principle detect explosives and biological weapons even if they are concealed in clothing, sealed packages, suitcases, etc since the THz radiation is readily transmitted through plastics, clothing, luggage, paper products, walls, and other non-conductive (non-metallic) materials. By comparing measured reflectivity (or transmitted) THz spectra with known calibration spectra, one may therefore identify the presence of these agents and distinguish them from objects such as keys, coins, human skin, and clothing. Since metals are relatively opaque to transmission of THz wavelengths and have a roughly constant reflection spectra, metal weapons such as handguns and knives are similarly identifiable by THz examination.

Most THz imaging systems proposed in the past have been based upon a single THz source and detector pair that are scanned across the object space to be imaged. These systems consequently take a significant amount of time (typically minutes) to acquire the data to generate a THz image of even a single small object (e.g. of approximately a few square centimeters), and are not suitable to real-time acquisition of THz images. Additionally, current state-of-the-art THz imaging is based on short-pulsed laser or continuous wave difference frequency THz generation and detection. The difficulty with extending either of these techniques to continuous wave THz imaging of coherent or incoherent THz radiation is that coherent continuous wave or short-pulsed laser sources are required. Moreover, the laser sources that generate and detect the THz radiation must retain a coherent phase relationship to each other. Using these methods, the imaging of an incoherent THz source is not possible. The present invention design and technique does not require a particular coherent or incoherent source of THz. It allows the flexibility to utilize an electronic THz source, a laser-based THz illuminating source, or incoherent ambient THz radiation which might be present, for example, from the sun.

An object of the present invention is to provide a spatial THz imaging technique which is capable of detecting multiple THz sources simultaneously within a wide field-of-view. To accomplish the same functionality with a single line of sight measurement, the line-of-sight has to be scanned across the field of view to be measured, which incurs the difficulties discussed above. By means of the present invention the spatial resolution is sufficient not only to determine that an explosive or biological agent is present, for example, but also the physical extent and location of the object. This information is difficult to determine with a line-of-sight technique. The THz imaging approach of the present invention has sufficient spatial resolution to detect explosives or biological agents that are concealed on a person or hidden in packages, containers or vehicles from a stand-off distance. A longer term advantage of the present invention is that it produces more information than that yielded by a single line-of-sight system. By obtaining multiple images over time one can apply imaging processing techniques to multiple images and multiple THz sources that can be used to reject noise and reduce false alarms in a complete system.

SUMMARY OF THE INVENTION

Now in accordance with the present invention THz imaging apparatus and methods are provided for rapidly and effectively examining a region of interest to determine the presence of specified compositions. The apparatus includes means for generating electromagnetic radiation of a desired terahertz frequency suitable for the examination, and for rendering the radiation incident at the region of interest. Detector means are provided at a plurality of points in a plane spaced from the region of interest, for detecting the terahertz radiation reflected from or transmitted through the region. Means are provided for converting the detected terahertz radiation to an image of the region of interest from which the presence of the specified compositions are determinable.

For routine, stand-off sensing, a wide area is illuminated with a bright THz source. The source can be broadband and incoherent (such as radiation from the sun) or narrow band and tunable. The transmitted or reflected THz radiation is then detected with a THz imaging array. A critical technical limitation to this approach has in the past been the lack of an imaging THz detector array (regardless of spatial resolution or tunability). Crudely speaking, the equivalent of a digital camera has not existed in the THz regime. The limitation in the THz regime has not been the "camera" lens but rather the detector array that digitizes the image.

The THz imaging array of the present invention is related to our previous work in radio astronomy. Unlike radio astronomy for which the positions and spectral content of the radio sources (stars) is not known before hand, the spectral content and location of sources is known for THz-based standoff detection of explosives/biological agents, but the THz transmission properties of the intervening objects needs to be determined.

In the present invention, the detector means may comprise a tunable interferometric array of spaced detectors. The signal outputs from pairs of the detectors are combined with proper delay and correlation in phase and quadrature to produce components for the Fourier transform plane corresponding to the detector plane. The detector array can include a plurality of semiconductor photomixers. Photomixer driving means comprising a frequency stabilized tunable optical heterodyne source are coupled to the photomixers by a common fiber optic connector. The array can comprise an in-line arrangement of detectors, and means for rotating the array about a fixed axis. The original brightness distribution at the region of interest are recovered by Fourier inversion of the Fourier components.

The photomixers can be photoconductive devices, wherein the driving means for each pair of such devices is a pair of lasers having a difference frequency which gates the photomixers, the incoming terahertz radiation at each member of the pairs of photomixers being mixed with the difference frequency to provide modified signal outputs at intermediate frequencies in order to facilitate signal processing.

The wide field-of-view THz imaging interferometer array used is capable of high spatial resolution and spectral resolution in the 0.2–10 THz range. This array can image multiple sources of coherent or incoherent THz light simultaneously without the need for expensive short-pulsed laser systems. The invention thus may include a continuous wave terahertz imaging spectrometer tunable from 0.2 to 3 THz in order to remotely detect, monitor and identify concealed explosives such as C4 and RDX. The system utilizes a high brightness THz source illuminating the region of interest and detected by the tunable THz interferometric imaging array. The THz imaging array has a wide field of view and high spatial resolution. While the system preferably uses a heterodyne photomixing detection technique, it may also use homodyne photomixing detection. The high-speed photomixing devices for heterodyne detection is preferably designed to operate at optimum intermediate frequencies. The photomixing devices can serve both as source and detectors. A database of required THz-frequency spectral signatures for target explosives is provided for use with the system, and neural network algorithms can also be conjunctively used to identify selected explosives from the THz images.

BRIEF DESCRIPTION OF DRAWINGS

The invention is diagramatically illustrated, by way of example, in the drawings appended hereto, in which:

FIGS. 1a and 1b are simplified schematic showings of two possible system implementations of the present invention.

FIG. 2 is a schematic diagram illustrating the phase of an incoming THz wavefront as measured at a pair of spaced detectors;

DESCRIPTION OF PREFERRED EMBODIMENTS

Figure 3:
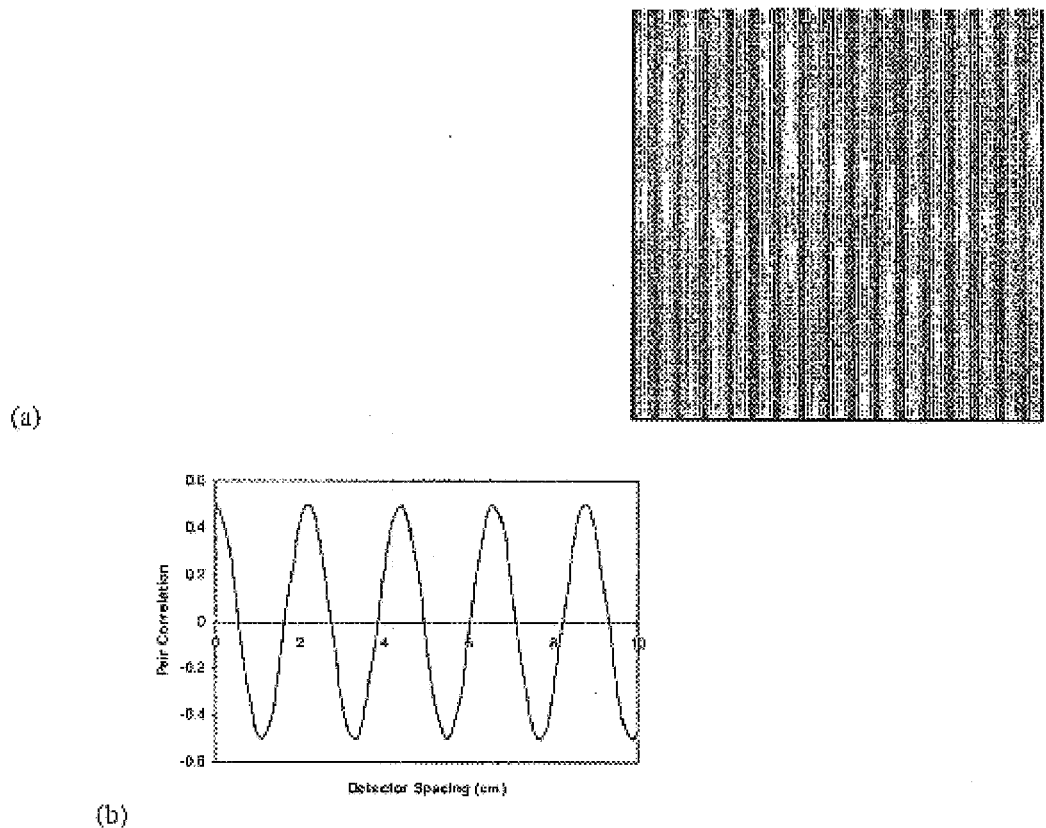
FIG. 3(a) is a photograph of a real-space image generated by a single detector pair at a fixed separation.
FIG. 3(b) is a graph depicting expected dependence of the correlated THz electric fields as measured by a detector pair as a function of the separation (baseline) of the detector pair. For this plot, $\alpha=10°$, $k=16.5$ cm$^{-1}$ (0.5 THz), and A=1.

For routine, non-intrusive screening of personnel, packages, or pallets entering an airport terminal, base, ship, or post office, personnel (or packages 8) can as shown in FIG. 1(a) be positioned or move between a THz source or sources 10 and a THz imaging array 12. The schematic of FIG. 1(a) is thus based on a transmission mode. In FIG. 1(b) the THz source 14 is rendered incident on spaced personnel and objects 13, and detection at imaging array 12 is by reflection. In both cases (a) and (b), THz sources illuminate the person, pallet, vehicle or other object under study.

An advantage of interferometric imaging compared to imaging with the equivalent of a digital camera is that interferometric imaging can be done with only a few individual detector elements. Consumer digital cameras typically have imaging arrays of 1024 by 768 pixels or 780,000 individual detector elements in the array. Such high density of detectors in the THz range is presently not technologically feasible. One reason is that conventional detectors in the 0.1–10 THz frequency range generally require liquid Helium cooling and are not easily integrated into dense array structures. In order to image in the THz range, therefore, one must generate images using only a few (1–20) detector elements. Interferometric imaging offers great advantage due to its ability to image with only a handful of detector elements, and its ability to image many sources of THz radiation at once, to image incoherent as well as coherent sources, and to provide spectral information as well as spatial imaging information.

The THz imaging array 12 used in the invention is related to technology known for use in radio astronomy. Unlike radio astronomy for which the positions and spectral content of the radio sources (stars) is not known beforehand, for a THz-based explosives monitoring system, the spectral content and location of sources is known, but the THz transmission (or reflection) properties of the intervening objects needs to be determined.

To perform imaging of THz in real time, a technique of radio interferometry is therefore utilized, where signals at two or more points in space (the aperture plane) are brought together with the proper delay and correlated both in phase and in quadrature to produce cosine and sine components of the brightness distribution. This technique thus measures both amplitude and phase of the incoming signal, and if measured from a sufficient number of points in the aperture plane, the original brightness distribution can be synthesized (imaged) through standard Fourier inversion. Constructing images with interferometric arrays is a technique that has been developed for use with astronomical imaging in both the radio and X-ray wavelength ranges. The radio range, from metric to sub-mm wavelengths, has been the traditional regime for development of the techniques of Fourier image reconstruction, and many tools exist to model and simulate the characteristics of interferometer arrays. Sparse arrays containing 3–10 elements require special treatment to reduce ambiguities (called sidelobes) in the reconstructed images. In radio astronomy several techniques for imaging with a sparse array are known, employing variations of frequency-synthesis (combining data at multiple frequencies to exploit the different spatial information at each frequency) that may be applied to the THz imaging problem if the data are obtained at different THz frequencies.

The THz system of the present invention includes three major components: (a) the THz interferometric imaging array, (b) the (preferably) heterodyne mixing of the THz signals and signal processing of the intermediate frequencies at 100 MHz and (c) a high brightness THz source.

Referring to FIG. 2, the imaging interferometer is similar to a phased array detector in that the difference in arrival times for a wavefront at two point detectors depends on the angle $\alpha$ of the wavefront 20 with respect to the two detectors. The angular resolution for a given wavelength $\lambda$ is determined by the separation d of the two detectors: $\theta = \lambda/d$ (radians). The field of view of the interferometer is determined by the smaller of the beam pattern (directionality) of the individual detectors and the bandwidth of the detectors. For a gaussian bandwidth, the angular sensitivity of the interferometer also decreases as a guassian. The 1/e width of the field of view is given by $W_{1/e} = c/\pi d\sigma$ (radians) where $\sigma$ is the 1/e bandwidth of the antennas. The field of view is roughly a factor of $v/\pi\sigma$ larger than the angular resolution. As an example, if THz antennas, which have a center detection frequency of 1 THz with a 1/e bandwidth of 0.01 THz, are spaced 10 cm apart, the interferometer can image a field of view of 5° with a resolution of 10'. For 1 cm spacing, the field of view is 51° with a resolution of approximately 1.70°.

As an example of the potential spatial resolution, if the THz imaging array (center frequency approximately 1 THz with a detector baseline distance of 1 cm, see Table 1) were mounted on a jeep approximately 15 m (50 ft) from a piece of explosives hidden on a person, the corresponding spatial resolution for that target explosive 15 m away would be approximately 45 cm at 1 THz and approximately 4.5 cm at 10 THz. Finer resolution (factor of 10) could be achieved with a 10 cm baseline array. This is sufficient resolution to identify a wallet size piece of explosives. The thickness of the explosive should be a few mm. At a distance of 50 m for wide area remote viewing, a 1 cm baseline array has a spatial resolution of 1.5 m while a 10 cm baseline array has a spatial resolution of about 15 cm.

TABLE 1

Estimated angular resolution of interferometer array as a function of frequency v and distance d.

| v (THz) | d (meters) | | | | |
|---|---|---|---|---|---|
| | 10 | 1 | 0.1 | 0.01 | 0.001 |
| 0.1 | 62" | 10' | 1.7° | 17° | 170° |
| 1.0 | 6.2" | 62" | 10' | 1.7° | 17° |
| 10.0 | 0.6" | 6.2" | 62" | 10' | 1.7° |

In the present invention the THz imaging array can among other suitable detectors, employ THz detectors manufactured by Picometrix of Ann Arbor, Mich. The Picometrix THz detectors operate as photoconductive devices. For these detectors, a gold microfabricated antenna structure is fabricated on top of low-temperature grown GaAs, which is a fast photoconductive material. They are fiber-optically coupled, room temperature detectors. For typical Picometrix detector design parameters, the THz imaging array's field-of-view is determined by the detectors' directionality. The detectors' field of view can be adjust (a few degrees to approximately 50 degrees) by slightly changing the design of the THz lens which focuses the THz radiation onto the detector.

The imaging interferometer consists of an array of individual detectors. A pair of such detectors 16, 18 is shown in the schematic depiction of FIG. 2. Each detector measures the amplitude and phase of incoming THz radiation. As a wavefront of THz radiation encounters the array, each pair of detectors (such as 16, 18) in the array measures one spatial Fourier component of the incoming THz radiation as determined by the separation of the detector pair. Each spatial Fourier component is represented by a point in the Fourier transform plane (the u-v plane). In order to determine a spatial Fourier component and consequently the direction of the incoming THz wavefront 20, the phase delay in the wavefront's arrival time between a pair of antennas must be measured. The relative angle between the direction to the source and the baseline (an imaginary line connecting the two antennas effectively comprising the detectors) defines the geometric delay $\tau_g$ in arrival of the wavefront between the two antennas. All the directions that form a cone around the baseline have the same phase delay $\tau_g = (b \cdot \sin\alpha)/c$, where b is the length of the baseline, c is the speed of light, and $\alpha$ is the relative angle. In order to determine the correct source direction additional measurements with other orientations of the baseline must be carried out.

For a fixed separation between the detector pair, one spatial Fourier component is measured. In real-space, this single Fourier component corresponds to intensity fringes as shown in FIG. 3(a). By changing the spacing between the detector pair (but keeping the distance to the source fixed, the spatial Fourier component changes resulting in a different spacing between the alternating light and dark fringes in FIG. 3(a). By adding together the images generated by different detector pair spacings, the composite real-space image is formed. A simple experimental verification of inteferometric detection can be conducted by varying the spacing between a detector pair (the distance b in FIG. 2). Based on this geometry, the expected correlation C between the THz signal from a point source detected at the two detectors will be $$C = \frac{A^2}{2}\cos[kb\sin(\alpha)]$$

where A is the amplitude of the incident THz plane wave, k is the wavenumber of the incoming electromagentic wave, b is the spacing between the detector pair, and $\alpha$ is the angle that the incoming wavefronts make with respect to the detectors as defined in FIG. 2. A plot of the expected experimental data is shown in FIG. 3(b) for a frequency of 0.5 THz. As the Fourier components of different detector pairs are included, the resulting image approaches the point spread function of the point THz source. The point spread function can be used, for example, to clean the THz interferometric images and remove the side lobe artifacts in the interferometric image.

Figure 4:
FIG. 4 is a schematic depiction of five detector antennas in an inline arrangement.

For a given number of detectors N, there are N(N−1)/2 possible pair combinations. It is desirable to place the antennas such that there is non-uniform spacing between them so that the Fourier plane is sampled as completely as possible. A typical in-line arrangement of five antennas, along with the resulting baselines is shown in FIG. 4. A log-periodic spacing is typical. By recording the correlation in electric field at the various combinations of detector pairs, information as to the spatial distribution of emission from the THz source can be generated. An image is generated from the spatial Fourier components of all the different pair combinations. The quality of the image depends on the coverage of the u-v plane that in turn depends on the arrangement of the detecting elements of the interferometer. The primary concern in designing the configuration of antennas is to obtain coverage of u-v plane uniformly and efficiently over a range determined by the required angular resolution. Efficient u-v plane coverage with a small number of detectors may be achieved using an in-line arrangement of detectors combined with a rotation of the array about a fixed axis. If measurements are made 20 times during the rotation of an N element array, the equivalent number of detectors is 20N. This can either lead to improved image quality or to a reduction in the number of required antennas in the array.

Figure 5:
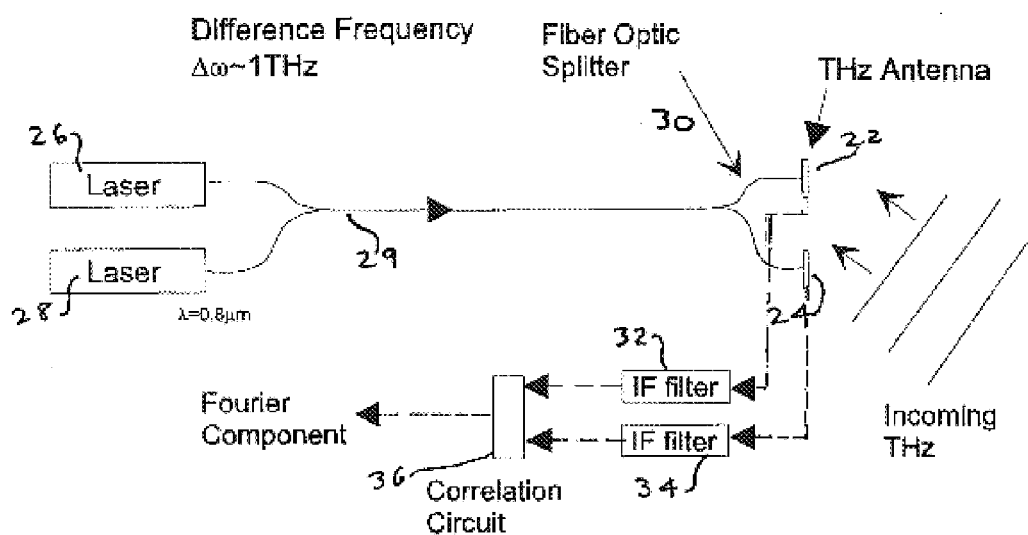
FIG. 5 is a schematic diagram depicting elements used in the invention to enable interferometric detection by heterodyne photomixing.

Referring to FIG. 5 interferometric detection of THz is effected by the fiber-optic coupled photoconductive antenna detectors a pair of which is shown at 22, 24. In these detectors, the incoming THz radiation is detected by mixing the incoming THz radiation with two infrared (~780 nm) laser beams from lasers 26, 28 which "gate" or "turn on" the photoconductive detectors. There are distinct advantages of coupling the infrared laser light to the detector structures using fiber optical cables 29 and splitter 30. For example, to combine the laser light and then distribute it to a larger number of detectors is straight forward using fiber couplers and star-splitters. In this manner, one could conceivably use only two infrared laser sources to power every antenna in an N-element interferometric array. Moreover, the fiber coupling makes the entire array more robust and reliable. By attaching the fibers to the detectors, they can be easily moved relative to each other (ie. an adjustable baseline or detector spacing) since the light delivery system is fiber optic. This design allows the possibility that the array can survey a wide area for evidence of explosives very quickly with low spatial resolution. If a particular region exhibits spectroscopic signatures of agents, the baseline of the array can be adjusted to examine the suspected area with higher spatial resolution.

Lasers 26, 28 are two narrowband infrared lasers which are used in conjunction with the detectors to detect THz radiation via difference frequency optical heterodyne photomixing. Two External Cavity Diode Lasers, (ECDLs), are used to produce two different colors (wavelengths) of infrared radiation near ~780 nm. The THz frequency can be tuned by adjusting the difference frequency of the two infrared colors. While homodyne detection of laser mixing in photoconductive antennas has been demonstrated by others, heterodyne detection has not to our knowledge been demonstrated. The heterodyne detection technique improves the sensitivity of the THz array compared to homodyne (DC) detection. Heterodyne detection decouples the THz source from the THz local oscillator (LO) meaning that the THz source and LO do not need to be coherent or derived from the same source. In the photo-mixing detection technique, the THz local oscillator is provided by the mixing of the two infrared laser wavelengths. Moreover, the heterodyne detection technique lends itself to scanning the local oscillator frequency thereby obtaining spectral as well as spatial images from the array.

In the photomixing geometry, one can conceptually think of the mixing of two infrared laser sources as generating a local oscillator (LO) signal within the photoconductive antenna detector element. In this geometry, the intermediate frequency produced by the mixing (beating) of the local oscillator and Terahertz signal could be in the 100–3000 MHz range (the linewidth of the ECDL source is approximately 5 MHz). The intermediate frequency at 100 MHz is processed since electronic components are readily available at this frequency. The relative phase and amplitude of the THz electric field for a pair of detectors (ie., Fourier component for u-v plane) is determined by correlating the measured intermediate frequency (IF) signal frequencies at the two detectors. Once the THz signals are downconverted to an IF band of 100 MHz, the signal can be handled with exactly the same, well-developed correlator technology used in radio astronomy.

In the heterodyne mixing technique used the incoming THz signal $\omega_{signal}$~1 THz) received by the individual detector is combined with the local oscillator signal $\omega_{LO}$ which differs from the signal frequency by a small amount. The local oscillator signal $[\omega_{LO}$~$(1+\delta)$ THz] is produced in the present embodiment of the imaging array by the difference frequency mixing of the CW IR laser beams. The output of the detector is the mixing of the two THz signals to the difference frequency $\omega_{IF}=\omega_{LO}-\omega_{signal}$. The difference frequency is in the intermediate frequency range (kHz–GHz) and can be electronically processed to retrieve the phase and amplitude of the THz signal. The relative phase and amplitude of the THz electric field for a pair of detectors (i.e. Fourier component for u-v plane) is determined by correlating the measured IF signal frequencies at the two detectors. By sweeping the local oscillator frequency (i.e. varying the wavelength difference between the two IR lasers) with a fixed IF frequency, the interferometer is capable of imaging the THz sources at various frequencies. The advantage of sweeping the LO frequency is to enable monitoring of a specific chemical component in the object under study and thereby identify explosives by their spectral characteristics in the THz range.

Figure 6:
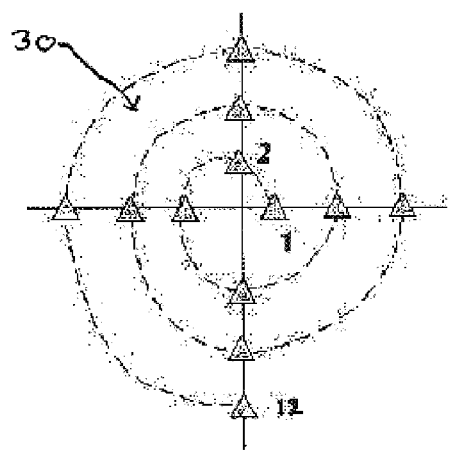
FIG. 6 is a schematic diagram depicting an arrangement of detector antennas for use in a rotational mode.

A typical arrangement of antennas for the interferometer is schematically shown in FIG. 6 that combines five individual antennas and utilizes rotation in order to illustrate the imaging of an interferometric THz array. A non-redundant arrangement of 12 detectors provides 66 Fourier components for every rotational orientation of the array 30. The chosen array design places a total of 12 detectors along two perpendicular axis of a geometric spiral as illustrated in figure. Each triangle represents a detector and each detector is numbered from 1 to 12 in a counter-clockwise fashion.

For efficient coverage of the Fourier Transform u-v plane, it is important to vary the spacing between each detector pair such that each pair produces a unique spatial Fourier component that is not a harmonic of any other component. Multiple occurrences of the same detector spacing would not yield any additional imaging information. The spacing of FIG. 5 is modeled by $$d=ar_ob^{(n-1)} \quad (1)$$

where d is the distance from the origin, a is the spacing constant, $r_o$ is the distance of the first detector, and n is the number of the detector. The value b is a constant that describes the rate at which the successive detectors spiral out from the origin. Having chosen b, the spacing constant a can be used as a multiplicative factor to normalize the overall size of the detector array for different applications. The overall size of the array can be estimated as roughly twice the distance from detector 12 to the origin ($d_{12}=ar_ob^{11}$).

If the imaging array were based on a spinning platform, the array's rotation relative to the THz source can be utilized to improve the image quality. If for example measurements are made 20 times during the rotation on an N element array, the equivalent number of detectors is 20N. This can lead to improved image quality or to a reduction in the number of required antennas in the array. Using the rotation of the array platform, a THz source can be located with only three antennas in the array. In effect, three antennas laid out in a triangular pattern can be used to triangulate the location of a THz source on space. Further improvements can be made by tuning relatively narrowband detectors to various THz wavelengths (as is possible using CW infrared laser excitation). In addition to giving spectral information concerning the THz source, the interferograms at various THz frequencies can be used to improve the spatial resolution or reduce the number of required antennas.

In producing images from array 30, the array is rotated about the origin to fill in more spatial Fourier components in the uv plane, adding to the overall resolution. Data is acquired from the array for every 1° of rotation for a total of 90°. In processing this data it can be assumed that the source of THz radiation is in the far field. In other words, the distance from the imaging array to the source is much larger than the typically spacing between the detectors in the array. In this limit, the wavefronts of the incoming THz radiation are planar.

The detection of concealed C4 or RDX explosives on persons or in packages is challenging since there are many other substances that reflect or transmit THz radiation. Metal, as an example coins and belt-buckles, etc. have a roughly constant reflection spectrum. The present system can distinguish centimeter sized C4 or RDX explosives from common items. RDX has a reflection spectrum that contains large peaks at certain THz frequencies that are distinguishable from other items such as clothing, skin, and metal.

To demonstrate the capability of the THz imaging array, we simulated the imaging of RDX and found that based on its spectroscopic signature, it can be distinguished from metallic items. For the simulation, the RDX was assumed to be 30 m away from the THz imaging array. The size of the array was 5 m. An image of two 1.4 cm square samples placed next to each other was obtained. One is RDX and the other is metal. A false color image was generated by coloring red any locations which had a large reflection at the 0.08, 0.175 and 0.4 THz characteristic frequencies of RDX. Otherwise, each individual frequency was assigned a color proportional to its THz frequency. Consequently, the metal (which reflects all THz frequencies) was colored white. The RDX was easily distinguished from the metal and the background. A neural network algorithm can be used to analyze the THz images as a function of frequency and to identify spatial locations that exhibit spectral characteristics of RDX.

There are several important differences between the arrays that are used for astronomical applications and those used in the present application for the detection of concealed weapons. For astronomical radio interferometric imaging, it is assumed that the incoming radio waves have planar wavefronts. With appropriate delays between the various detector elements, any pair of elements can sample the electric field from the same wavefront. When the same wavefront is sampled, even an incoherent source of radiation can be detected interferometrically since by definition all points on the same wavefront have the same phase (spatially coherency). For the application to the detection of explosives, the baseline (spacing between array elements) is estimated to be ~10 cm. The distance between the THz source and detecting array would be only on the order of a few meters for portal-type detection to about 50 meters for wide area detection. While distances of 2–50 meters are a few orders of magnitude larger than the spacing between the array elements, the THz interferometric array will have to contend with partially curved, not planar, wavefronts. Moreover, since the wavefronts are curved, it is much more problematic to image an incoherent source of THz radiation since the appropriate delays between detector elements depend on the wavefront's curvature.

This potential technical problem is overcome by using THz source radiation that has a sufficiently long coherence length. The THz radiation that is generated by optical heterodyne difference frequency mixing has a very long coherence length since the ECDL Lasers that generate the THz have very long coherence lengths. Using a long coherence length THz source means that many sequential wavefronts are coherent and will easily produce an interferometric signal. This design constraint puts coherence length limits on the type of THz sources that could be imaged.

In astronomical applications, the location, physical extent, and frequency content of the THz source (e.g., stars) is not known. The radio interferometric array and data processing is designed to determine the location and spectral content of the radio sources. For the present invention, the location, physical extent and spectra of the THz sources are well-known since they are part of the imaging system. Instead, the interest is in the THz transmission or reflection spectra of the intervening material: ie. are explosive or biological agents present? In order to process the THz images for the presence of explosives or biological agents, images at characteristic THz frequencies are acquired by changing the frequency of the THz local oscillator. Artificial neutral network (ANN) algorithms can be used to determine the presence of explosives and biological agents from the THz images. An ANN is a collection of mathematical functions that constitute a mapping of inputs into outputs. In the present invention, the inputs are spectral image arrays derived from the THz interferometric imaging system. The outputs are positive identification as well as location within the detection area of target agents. Using values for the detected power at specific THz frequencies as inputs, the neural network can be "trained" to recognize that the presence of different combinations of THz colors (eg. frequencies) that correspond to specific explosives or biological agents. This type of use for ANN's is well known. For example ANNs have been used to establish a hierarchy for classifying almost 150 strains of micro-organisms based on Fourier Transform-Infrared (FTIR) absorption spectra. (T. Udelhoven, et al., "Development of a Hierarchical Classification System with Artificial Neural Networks and FT-IR Spectra for the Identification of Bacteria," *Applied Spectroscopy*, 54, no. 10, p. 1471 (2000)). Similarly, individual organic components within a multi-species mixture of chlorinated hydrocarbons have been identified with high accuracy from low signal-to-noise ratio Raman spectra through the use of ANNs. (T. Lu and J. Lerner, "Spectroscopy and Hybrid Neural Network Analysis," *Proc. IEEE*, 84, no. 6, p. 895 (1996)). Neural Network principles have similarly been used with THz spectra as an analysis tool to distinguish different sets of DNA. (T. Globus, et. al "Application of Neural Network Analysis to Submillimeter—wave vibrational spectroscopy of DNA macromoledules", in the Proceedings to the 2001 ISSSR, June 12–15, Quebec City, Canada (2001)). Artificial neural networks can be used in the present invention to analyze combined images taken at either different times or taken with different spatial resolutions to reduce false alarm rates.

In the present invention as shown in the schematic of FIG. 5, the method for detecting (and generating) THz radiation is the optical mixing of two CW infrared laser beams by photoconductive antenna structures. The frequency difference of two external cavity diode lasers (ECDL) is tuned to approximately 1 THz corresponding to 33 cm$^{-1}$ (Far-Infrared Region). The ECDL's have a center wavelength of 780 nm and a tuning range of ±9 nm corresponding to ±4.2 THz. The ECDL lasers have excellent stability (Line width approximately 5 MHz) which allows scanning of their difference frequency through 0.1–2 THz. ECDL lasers are chosen over less expensive DFB and diode lasers due to the ECDL's flexibility and ease of tuning. The output of the lasers are combined in a fiber coupler 29. The power of the combined laser beams is split using a fiber-optic splitter 30 and directed onto the two detecting antennas 22, 24 comprising one of the pairs of spaced detectors using fiber optic cables. The optical mixing of the incoming THz and infrared lasers generates an electrical signal at an intermediate frequency $\omega_{IF}$. The spatial Fourier component of an antenna pair is measured by filtering out a band of IF frequencies at filters 32, 34, and then using a correlation circuit 36. As the THz detectors, photoconductive detectors can be used, such as those fabricated by Picometrix as previously mentioned.

The two laser sources are thus tuned to a difference frequency ($\Delta\omega$) in the THz range. The combined laser beams are split using a fiber splitter and then directed onto the photoconductive antennas for detection of incoming THz radiation by optical mixing With use of heterodyne detection the intermediate frequency of the mixed THz frequencies is in the MHz range rather than the typical DC or KHz range of homodyne detection. [For standard THz spectroscopy setups using short-pulse laser sources, the laser beam or applied voltage to the THz radiator is modulated at KHz repetition rates to facilitate phase-sensitive detection using lock-in amplifiers.] The THz detector electronics are designed so that their antenna detector packages are capable of transmitting intermediate frequencies in the 100 MHz range.

Figure 7:
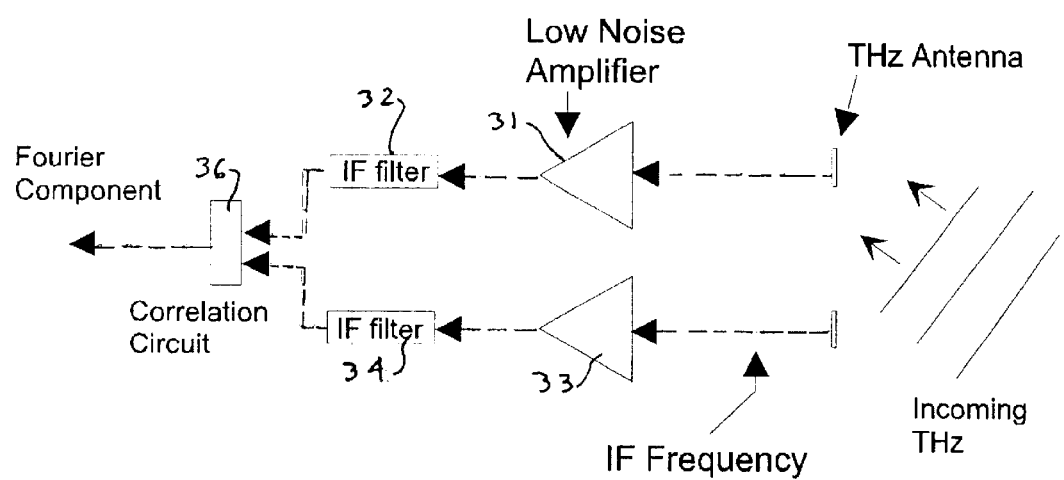
FIG. 7 is a schematic diagram depicting the arrangement of the intermediate frequency electronics utilized to process the detector outputs in the invention.

As seen in FIG. 7, after mixing the THz signal down to an intermediate frequency (IF), extremely good filters 32, 34 and low-noise amplifiers 31, 33 in the 0.01 to several GHz range are used, since this frequency range is of great importance to wireless communications (as a baseband) and to optical communications (as a sideband). The intermediate frequency is processed at 100 MHz since electronic components are readily available at this frequency. The first step is to digitize the incoming IF band, sampling at the Nyquist frequency (1 Gsample/s for a 100 MHz bandwidth). The digital signal is then passed through a time-demultiplexer (a shift register), and each bit of the shift register is correlated (multiplied) with the corresponding bit from a second THz detector. A signal sampled at 1 GHz can be slowed to 125 MHz by use of an 8-bit time demultiplexer, and then passed to a 125 MHz Field Programmable Gate Array (FPGA) for correlation. This arrangement offers N=64 lags (8×8), which offers a frequency resolution for bandwidth B=100 MHz of $\Delta f=2B/N,=15.6$ MHz. A higher number of lags can be achieved by cascading correlator chips, which result in higher frequency resolution. Considering this as one correlator unit, each correlator unit processes the signals from one pair of detectors. For n detectors, n(n−1)/2 correlator units are needed.

Since THz sources/detectors/components are a very active arena of research, in the future it is possible that THz components may be developed which are superior to the components discussed here. However, the overall design of the THz imaging array is very robust: (a) as long as the newer detecting elements detect the THz electric field rather than power (as will be the case for any new THz mixer and THz local oscillator), that new mixer technology could be used to improve the THz imaging array performance (b) the THz sources to be imaged can be either incoherent or coherent. This is actually a systems engineering advantage for the THz interferometric array approach. The interferometric array design can easily incorporate advances in THz local oscillator sources and mixers without having to totally reinvent a THz array with each advance in THz technology.

While the invention has been set forth in terms of specific embodiments thereof, it is to be understood in view of the disclosure that numerous variations upon the invention are now enabled to those skilled in the are, which variations yet reside within the teachings herein. Accordingly the invention is to be broadly construed and limited only by the scope and spirit of the claims now appended hereto.

What is claimed is:

1. Terahertz imaging apparatus for examining a region of interest to determine the presence of a specified composition; comprising:
   (a) means for generating electromagnetic radiation of a desired terahertz frequency suitable for said examining;
   (b) means for rendering said terahertz radiation incident at said region of interest;
   (c) detector means comprising an interferometric array of spaced detectors for simultaneously detecting at a plurality of points in a detector plane spaced from said region of interest the terahertz radiation reflected from or transmitted through said region; and
   (d) means for converting the said detected terahertz radiation to an image of said region of interest from which the presence of said specified composition is determinable.

2. Apparatus in accordance with claim 1, including means for combining the signal outputs from pairs of said detectors with proper delay and correlation in phase and quadrature to produce components for the Fourier transform plane corresponding to said detector plane.

3. Apparatus in accordance with claim 2, wherein said detector array comprises a plurality of semiconductor photomixers; and further including photomixer driving means.

4. Apparatus in accordance with claim 3, wherein said photomixer driving means comprises a frequency stabilized tunable optical heterodyne source coupled to said photomixers by a common fiber optic connector.

5. Apparatus in accordance with claim 3, further including means for synthesizing the original brightness distribution at the region of interest by Fourier inversion of the said Fourier components.

6. Apparatus in accordance with claim 5, further including image analyses means for comparing portions of the imaged region of interest with test standards to determine the presence of said specified compositions.

7. Apparatus in accordance with claim 5, wherein said analysis means compares said portions with a test standard corresponding to an explosive composition.

8. Apparatus in accordance with claim 5, wherein said analysis means compares said portions with a test standard corresponding to a biological agent.

9. Apparatus in accordance with claim 3, wherein said photomixers are photoconductive devices, and wherein said driving means for each pair of photomixers comprise a pair of lasers having a difference frequency which gates said photomixers, the incoming terahertz radiation at each member of a said pair of photomixers being mixed with said difference frequency to provide modified signal outputs at intermediate frequencies to facilitate signal processing.

10. Apparatus in accordance with claim 2, wherein said detector array comprises an in-line arrangement of detectors.

11. Apparatus in accordance with claim 10, and further including means for rotating the array about a fixed axis.

12. Apparatus in accordance with claim 2, further including means for synthesizing the original brightness distribution at the region of interest by Fourier inversion of the said Fourier components.

13. Apparatus in accordance with claim 12, further including image analyses means for comparing portions of the imaged region of interest with test standards to determine the presence of said specified compositions.

14. Apparatus in accordance with claim 12, wherein said analysis means compares said portions with a test standard corresponding to an explosive composition.

15. Apparatus in accordance with claim 12, wherein said analysis means compares said portions with a test standard corresponding to a biological agent.

16. A Terahertz imaging method for examining a region of interest to determine the presence of a specified composition; comprising:

(a) generating electromagnetic radiation of a desired terahertz frequency suitable for said examining;

(b) rendering said terahertz radiation incident at said region of interest;

(c) by means of an interferometric array of spaced detectors simultaneously detecting at a plurality of points in a detector plane spaced from said region of interest the terahertz radiation reflected from or transmitted through said region; and (d) converting the said detected terahertz radiation to an image of said region of interest from which the presence of said specified composition is determinable.

17. A method in accordance with claim 16, wherein the signal outputs from pairs of said detectors are combined with proper delay and correlation in phase and quadrature to produce components for the Fourier transform plane corresponding to said detector plane.

18. A method in accordance with claim 17, wherein the original brightness distribution at the region of interest is synthesized by Fourier inversion of the said Fourier components.

19. A method in accordance with claim 18, wherein the region of interest contains an explosive composition.

20. A method in accordance with claim 18, wherein the region of interest contains a biological agent.

* * * * *